(12) United States Patent
Ralhan

(10) Patent No.: US 6,627,401 B2
(45) Date of Patent: Sep. 30, 2003

(54) METHOD FOR DETECTING A SINGLE NUCLEOTIDE POLYMORPHISM IN P21$^{WAF1/CIP1}$ GENE AS AN INDICATOR OF RISK OF ESOPHAGEAL CANCER

(75) Inventor: Ranju Ralhan, New Delhi (IN)

(73) Assignees: Council of Scientific and Industrial Research, New Delhi (IN); All India Institute of Medical Sciences, New Delhi (IN)

( * ) Notice: Subject to any disclaimer, the term of this patent is extended or adjusted under 35 U.S.C. 154(b) by 0 days.

(21) Appl. No.: 09/749,778

(22) Filed: Dec. 28, 2000

(65) Prior Publication Data

US 2002/0137040 A1 Sep. 26, 2002

(51) Int. Cl.$^7$ ............................ C12Q 1/68; C12P 19/34; C07H 21/02; C07H 21/04
(52) U.S. Cl. ................. 435/6; 435/91.2; 435/91.1; 536/23.5; 536/24.31; 536/24.33
(58) Field of Search .................... 435/6, 91.1, 91.2; 536/23.1, 24.1

(56) References Cited

PUBLICATIONS

Bahl et al. Nature–Oncogene (Jan. 20, 2000) 19 (3) 323–8.*
Ralhan et al. Clinical Cancer Research vol. 6, 2440–2447.*
Wang et al. PNAS vol. 94, pp. 14,590–14,595, Dec. 1997.*

* cited by examiner

Primary Examiner—Carla J. Myers
Assistant Examiner—Sally A Sakelaris
(74) Attorney, Agent, or Firm—Smith, Gambrell & Russell, LLP

(57) ABSTRACT

The present invention relates to analysis of the alterations in p21$^{waf1/cip1}$ gene and its expression in relation to p53 status in esophageal cancer, a method for screening of subjects having or at risk of having esophageal cancer by detection of the polymorphism in p21$^{waf1/cip1}$ gene, and use thereof as a diagnostic marker.

7 Claims, 1 Drawing Sheet

(1 of 1 Drawing Sheet(s) Filed in Color)

METHOD FOR DETECTING A SINGLE NUCLEOTIDE POLYMORPHISM IN P21$^{WAF1/CIP1}$ GENE AS AN INDICATOR OF RISK OF ESOPHAGEAL CANCER

FIELD OF THE INVENTION

The present invention relates to a novel single nucleotide polymorphism (SNP) in p21$^{waf1/cip1}$ cyclin dependent kinase inhibitor gene and its association with cancer. More specifically, p21$^{waf1/cip1}$, an important regulator of the cell cycle, binds to PCNA and acts as a mediator of growth suppressing and apoptosis promoting functions of p53.

BACKGROUND OF THE INVENTION

The citations noted in this application form a part of this disclosure, and are incorporated herein by reference.

Initiation, progression and completion of the cell cycle are regulated by various cyclins and cyclin-dependent kinases (CDKs), which are critical for cell growth. Genetic alteration and deregulation of CDKs and their regulators is closely associated with abnormal proliferation. Tumour development is intricately linked to increased cell proliferation or decreased apoptosis (programmed cell death). The human p21$^{waf1/cip1}$ localized to the chromosome 6p21.2 encodes a cyclin dependent kinase inhibitor, unregulated by wild type tumor suppressor protein p53, whose cellular level is elevated by genotoxic stress leading to either cell cycle arrest or cell death (Gujuluva et al., 1994; El-Deiry et al., 1995). Alterations in p21$^{waf1/cip1}$ may adversely affect the regulation of cellular proliferation and increase the susceptibility to cancer. p21$^{waf1/cip1}$ polymorphisms have been observed in various human cancers. The polymorphic variants have been reported to occur more frequently in cancer patients than in healthy individuals suggesting a role in increased susceptibility for the development of some types of cancers Mousses et al., 1995; Facher et al., 1997).

Although some polymorphisms have been identified in the p21$^{waf1/cip1}$ gene, there is a continuing need in the art to search for novel, hitherto unobserved, alterations, which may be useful in predicting susceptibility to cancer and can lead to new diagnostic and therapeutic tools. The goal of this study was to analyze the alterations in p21$^{waf1/cip1}$ gene and its expression in relation to p53 status in esophageal squamous cell carcinoma, and determine their relevance in predicting predisposition to cancer and potential as a molecular diagnostic marker.

OBJECTS OF THE INVENTION

The main object of the invention is to provide a method for screening subjects having risk or at risk of having oesophageal cancer by analysis of a p21$^{waf1/cip1}$ gene polymorphism.

Another object of the invention is to provide a useful target for linkage analysis and disease association studies.

Yet another object of the invention is to provide a method for identifying the wild type and codon 149 polymorphic variant.

Another object of the invention is to provide a method to analyze the alteration in p21$^{waf1/cip1}$ gene and its expression in relation to p53 status in esophageal carcinoma.

Yet another object is to study the relationship of p53 status in esophageal carcinoma and determine its relevance in predicting pre-disposition to cancer.

Yet another object is to develop a novel molecular diagnostic marker useful in the detection of esophageal carcinoma.

Still another embodiment of the invention is to screen for novel drugs that target the variant gene product.

SUMMARY OF THE INVENTION

The present invention relates to analysis of the alterations in p21$^{waf1/cip1}$ gene and its expression in relation to p53 status in oesophageal cancer, a method for screening of subjects having or at risk of having esophageal cancer by detection of the polymorphism in p21$^{waf1/cip1}$ gene, and use thereof as a diagnostic marker.

BRIEF DESCRIPTION OF THE DRAWING

The file of this patent contains a drawing executed in color. Copies of this patent with the color drawing will be provided by the Patent and Trademark Office upon request and payment of the necessary fee.

DETAILED DESCRIPTION OF THE INVENTION

Figure 1:
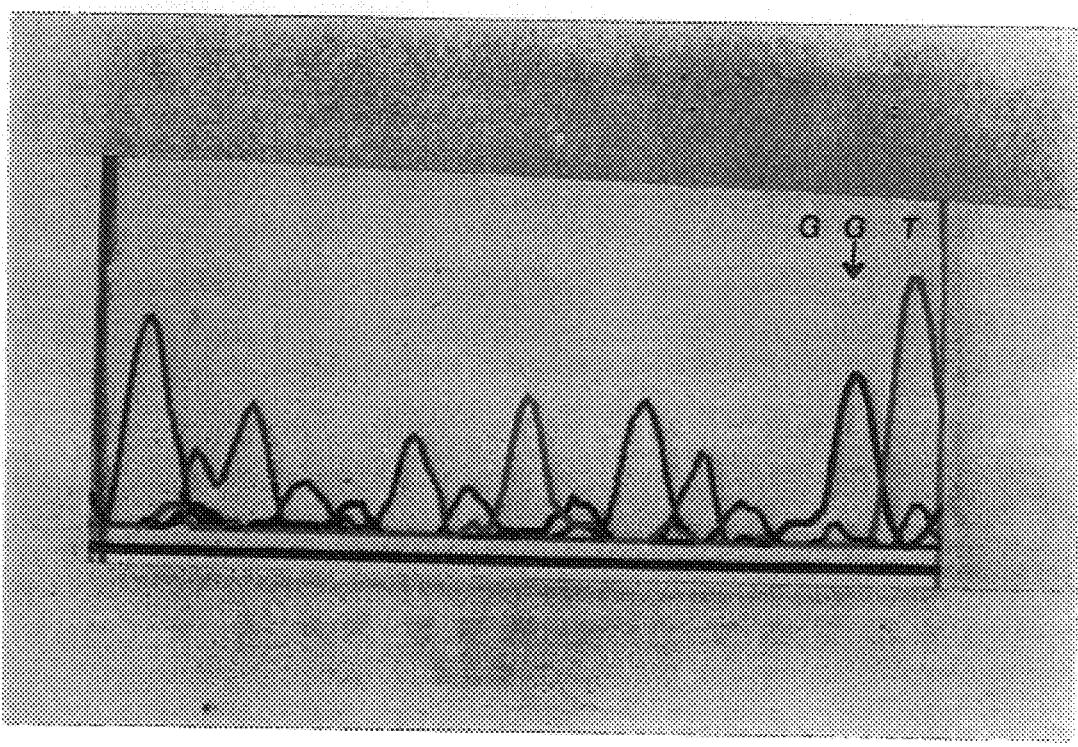
FIG. 1 illustrates nucleotide chains.

The p21$^{waf1/cip1}$ gene is transcriptionally activated by p53 and is responsible for the p53-dependent checkpoint that results in G$_1$-arrest after DNA damage (El-Deiry et al., 1993; Harper et al., 1993; Xiong et al., 1993).

A unique ability to associate with proliferating cell nuclear antigen (PCNA), an auxiliary factor for DNA polymerase δ and ε, distinguishes it from other cyclin dependent kinase inhibitors (CDKIs). The p21$^{waf1/cip1}$ gene encodes a 21 kDa protein, with two protein binding domains, a N-terminal domain which binds and inhibits cyclin-CDK complexes and a short sequence near the C-terminus which binds to proliferating cell nuclear antigen (PCNA) resulting in the inhibition of DNA replication (Xiong et al., 1993, Chen et al, 1995). While its ability to inhibit cyclin-CDK complexes resulting in G$_1$ cell cycle arrest is well established, the genetic alterations of p21$^{waf1/cip1}$ motif responsible for its binding with PCNA and the consequences of p21$^{waf1/cip1}$-PCNA interaction on cell cycle progression have not been completely understood. Expression of p21 inhibits PCNA-dependent DNA replication and mismatch repair in vitro and can suppress tumor growth suggesting its role as a tumor suppressor gene (Flores-Rozes et al., 1994; Li et al., 1994; Waga et al., 1994). It has been reported that cells deficient in p21 display a significantly different response to DNA-damaging agents than cells with an intact p21-dependent checkpoint. Cancer cells with an intact p21-dependent checkpoint undergo a G$_1$ arrest after DNA damage caused by ionizing radiation or chemotherapeutic drugs, whereas cells with a defective p21 response undergo apoptosis. Detailed analyses have demonstrated that the apoptosis is apparently induced by an uncoupling between mitosis and S phase after DNA damage. Instead of undergoing coherent arrest, cells without the p21-dependent checkpoint continue to undergo rounds of DNA synthesis in the absence of mitosis, culminating in apoptosis. Recently, it was demonstrated (Tian et al., 2000) that loss of p21 in human colon cancer cells resulted in a tremendous enhancement of radiation-induced apoptosis and was associated with improved radiocurability when the same cells were grown as s.c. tumors in nude mice. Alterations in p21$^{waf1/cip1}$ may therefore adversely affect the regulation of cellular proliferation and increase susceptibility of the subject to cancer.

Mutations and deletions of p21$^{waf1/cip1}$ gene have been rare in human cancers, suggesting that p21$^{waf1/cip1}$, if involved in tumorigenesis, may be exerting itself mainly on the expression level rather than on the gene level (Shiohara et al., 1994; Heinzel et al., 1996). However, p21$^{waf1/cip1}$ polymorphisms have been observed in various cancers. The polymorphic variants have been reported to occur more frequently in cancer patients than in healthy individuals, suggesting a role in increased susceptibility for the development of some types of cancers (Mousses et al., 1995; Heinzel et al., 1996; Facher et al., 1997).

Analysis of p21$^{waf1/cip1}$ gene polymorphism in ESCC patients and normal controls is discussed below.

Genetic analysis of p21$^{waf1/cip1}$ was carried out in ESCC (n=50) matched esophageal normal tissues and lymphocytes from ESCC patients as well as normal individuals (n=50). PCR amplification of genomic DNA using exon 2 specific primers produced a 450 bp fragment which was subsequently sequenced. No somatic mutations were identified.

The applicant, during the course of investigation, has found a novel single nucleotide polymorphism (SNP) in p21$^{waf1/cip1}$ cyclin dependent kinase inhibitor gene and its association with cancer. p21$^{waf1/cip1}$, an important regulator of the cell cycle, binds to PCNA and acts as a mediator of growth suppressing and apoptosis promoting functions of p53. Herein, a hitherto unobserved polymorphism in the carboxy terminal domain (codon 149, GAT→GGT) of the p21 gene, the domain involved in PCNA binding, is described in esophageal squamous cell carcinomas (ESCCs) in a significantly higher frequency in comparison with normal individuals. The resultant amino acid substitution from Aspartate to Glycine may have vital implication in PCNA mediated cell cycle regulation by p21$^{waf1/cip1}$. Interestingly, the frequency of p21$^{waf1/cip1}$ variants (codon 149) in ESCCs with wild type p53 was significantly higher than in tumors with p53 mutations suggesting that this polymorphism affects the p53 pathway and may play an important role in esophageal tumorigenesis. Analysis of p21$^{waf1/cip1}$ expression in relation to p53 gene and protein status revealed its induction by p53-dependent as well as p53-independent pathways in esophageal tumorigenesis. The Asp 149 p21$^{waf1/cip1}$ variant-PCNA (protein—protein) interaction provides a good model target for designing therapeutic agents for cancer treatment.

To describe specifically, the applicant has found a novel polymorphism at codon 149, involving a single nucleotide substitution, resulting in an A→G transition (GAT→GGT), thereby changing the predicted amino acid from aspartate to glycine, as shown in FIG. 1. The detection of Asp/Gly substitution in ESCCs, paired normal esophageal tissues and lymphocytes in 42 of 50 cases (84%) suggests the occurrence of a novel polymorphism in the p21$^{waf1/cip1}$ gene. The occurrence of this polymorphism was also observed in 8/50 (16%) normal individuals in the Indian population, eventhough its frequency was significantly higher in ESCC patients (p<10$^{-6}$, with an odds ratio of 27.56 and 95% confidence interval=8.49, 94.98). To understand the plausible role and biological significance of p21$^{waf1/cip1}$ polymorphism in the process of esophageal tumorigenesis, the applicant has sought to determine whether codon 149 variant is differentially distributed in ESCCs, where the p53 mutational spectrum had been determined by PCR-SSCP and direct DNA sequencing of exons 5–9 of p53 gene (Gaur et al., 1997; Ralhan et al., 1999). The association between a polymorphism of p21$^{waf1/cip1}$ and esophageal cancer provides the basis for developing methods and kits for diagnosing subjects. Of the 34 ESCC cases analyzed, 15 cases had wild-type p53. It is interesting to note that most of the wild-type p53 cases showed p21$^{waf1/cip1}$ polymorphism at codon 149, reflecting a significant association between codon 149 p21$^{waf1/cip1}$ variant and wild-type p53 (p=0.009).

The intriguing feature of the study was the alteration at codon 149 observed in the carboxy-terminal domain of the p21$^{waf1/cip1}$ gene which is involved in its binding to PCNA. The binding of p21$^{waf1/cip1}$ to PCNA has been shown to result in $G_1$ and $G_2$ cell cycle arrest in p53-deficient cells (Cayrol et al., 1998). The PCNA binding motif is located in the carboxy-terminal part of the p21$^{waf1/cip1}$ protein between residues 144–151 (Chen et al., 1995; Gobin and Ducommun, 1995; Nakanishi et al., 1995). Alterations in this region resulting in structural changes in the protein product are therefore likely to lead to differences in binding to PCNA, which is required for DNA replication and repair. Crystal structure studies of human PCNA complexed with a 22 residue PCNA binding peptide containing this motif have revealed that the p21$^{waf1/cip1}$ carboxy-terminal domain interacts with the inter-domain connector loop of PCNA and is likely to prevent the interaction of PCNA with other components of polymerase assembly (Gulbis et al., 1996). The PCNA binding site overlaps the nuclear localization signal (residues 140–156) and the C-terminal cyclin binding site. Either the N-terminal CDK or the C-terminal PCNA binding region of p21$^{waf1/cip1}$ is sufficient to inhibit DNA replication when expressed in cells (Chen et al., 1995; Luo et al., 1995). The C-terminal domain of p21$^{waf1/cip1}$ might inhibit cell cycle progression independently of the N-terminal CDK inhibitory domain and thus contribute to the antiproliferative activity of p21$^{waf1/cip1}$ (Luo et al., 1995; Nakanishi et al., 1995).

In a recent study, p21$^{PCNA}$-variant was created by changing the amino acids at codons 147 (methionine), 149 (aspartic acid) and 150 (phenylalanine) to alanine and the consequent structural changes were shown to abolish p21$^{waf1/cip1}$/PCNA interaction resulting in both $G_1$ and $G_2$ arrest (Cayrol et al., 1998). The ability of p21$^{waf1/cip1}$ to induce $G_1$ and $G_2$/M cell cycle blocks in p53-deficient DLD1 human colon cancer cells was due to p21$^{waf1/cip1}$/PCNA interaction and not its association with CDKs. Thus, PCNA is the primary target of p21$^{waf1/cip1}$ mediated growth inhibition in DLD1 colon cancer cells, and alterations in p21$^{waf1/cip1}$ C-terminal domain, especially at codons 147–151, can affect the cell cycle regulation by p21$^{waf1/cip1}$ (Cayrol et al., 1998). The A→G transition (GAT→GGT) at codon 149, manifested as a substitution of aspartate by glycine observed in the present study, will change the net charge of this domain, which may alter the molecular conformation and thereby inhibit the p21$^{waf1/cip1}$/PCNA interaction. the p21$^{waf1/cip1}$/PCNA protein—protein interaction provides a good model target for designing therapeutic agents for cancer therapy. The investigation of formation of complexes between PCNA and peptides derived from the C-terminus of p21 (141–160) at the molecular level revealed that residues 141–152 of the above peptide is the minimum recognition motif required for PCNA binding (Zheleva et al.) Ala mutation of Asp 149 significantly decreased the level of the PCNA binding and the inhibition of SV40 DNA replication (Zheleva DI et al., Biochemistry 2000 27: 39(25), 7388–97). Therefore, the applicant believes that the novel p21$^{waf1/cip1}$ polymorphism at codon 149 may influence the antiproliferative activity of p21$^{waf1/cip1}$ and account for increased susceptibility for development of cancer in individuals harboring this polymorphic variant. The data obtained in a parallel study in the applicant's laboratory exhibiting Asp/Gly polymorphism at codon 149 in betel and tobacco related oral squamous cell carcinomas in the Indian population may be of immense relevance in context to the current observation (Ralhan et al., 2000). Taken together, these data suggest that p21$^{waf1/cip1}$ polymorphism may play a role in increased susceptibility for the development of some types of cancer. The putative role of p21$^{waf1/cip1}$ polymorphism in esophageal tumorigenesis is further supported by the observation that the majority of the ESCCs having wild type p53 showed p21$^{waf1/cip1}$ polymorphism at codon 149 suggesting that this polymorphism influences p21$^{waf1/cip1}$ function in such a way as to obviate the requirement for p53 mutations to deregulate the cell cycle. A similar inference has been drawn for p21$^{waf1/cip1}$ polymorphism at codon 31, and a C→T transition 20 nucleotides downstream of the stop codon in the 3'UTR, from the observation that these polymorphic variants were under-represented in breast cancer and sarcoma patients, whose tumors possessed somatic p53 mutations compared to those without mutations, suggesting that they influence p21$^{waf1/cip1}$-mediated cell cycle regulation in a p53 independent manner (Mousses et al., 1995). However, the codon 31 polymorphism was infrequent in ESCCs in Indian population (Bahl et al 2000). The applicant has identified hitherto unobserved single nucleotide polymorphism (SNP), the common DNA variant in humans that represents a valuable resource for the genetic analysis of cancer. The SNP resides in the carboxy terminal domain of p21$^{waf1/cip1}$ gene, encoding the PCNA binding motif, in the codon 149 (G<u>A</u>T→G<u>G</u>T).

In short, the invention provides a novel method for screening of subjects having or at risk of having esophageal cancer by analysis of single nucleotide polymorphism in p21$^{waf1/cip1}$ gene, the method comprising the steps of:

(a) amplifying a target nucleic acid in DNA isolated from a specimen of a subject by polymerase chain reaction (PCR) using specific oligonucleotide primers;

(b) purifying the PCR products using agarose gels;

(c) DNA sequencing of the purified PCR products using both forward and reverse primers; and (d) detecting SNP in p21$^{waf1/cip1}$ gene by determining codon 149, G<u>A</u>T→G<u>G</u>T transition, and by observing the presence or absence of the codon 149 polymorphic variant, wherein the presence of the polymorphism is indicative of risk of cancer.

The method described above can be used to detect SNP in p21$^{waf1/cip1}$ gene; i.e. polymorphism of codon 149 (G<u>A</u>T→G<u>G</u>T) transition, Asp→Gly, and detects the presence or absence of the codon 149 polymorphic variant, wherein the presence of the polymorphism is indicative of risk of cancer.

In one embodiment, the target nucleic acid is DNA.

In another embodiment, the reagents are oligonucleotides.

In still another embodiment, the target nucleic acid is amplified prior to detection.

In yet another embodiment, the amplification is done by polymerase chain reaction (PCR).

In still another embodiment, the specimen is blood, normal tissue and tumor tissue.

As said earlier, the codon 149 G<u>A</u>T→G<u>G</u>T transition is manifested as an amino acid substitution, of aspartate to glycine. Alterations in this region, resulting in structural changes in the protein product, are likely to lead to differences in binding to PCNA, which is required for DNA replication and repair. The codon also resides in the nuclear localization signal (NLS) domain of p21$^{waf1/cip1}$.

The p21$^{waf1/cip1}$ variant protein can be detected. Accordingly, the method for detection of p21$^{waf1/cip1}$ variant protein comprises the steps of:

(a) determining the amino acid sequence of the said p21$^{waf1/cip1}$ variant protein; and (b) comparing the amino acid sequence of the said p21$^{waf1/cip1}$ variant protein with the wild type p21$^{waf1/cip1}$ protein and identifying the alteration in the said amino acid.

It is the finding of the applicant that the said Asp→Gly substitution occurs in the PCNA binding domain of the p21$^{waf1/cip1}$ variant and may influence the antiproliferative activity of p21$^{waf1/cip1}$, or result in a defect in DNA repair and account for increased susceptibility for development of cancer in subjects harboring this polymorphic variant.

In another embodiment, the p21$^{waf1/cip1}$-PCNA (protein—protein) interaction provides a good model target for designing therapeutic agents for cancer therapy. The method comprises the steps of:

(a) competitive PCNA-p21 peptides (141–160) binding assay to be used for screening compounds that could modulate PCNA-p21$^{waf1/cip1}$ interaction; and (b) using this assay, rationally designed peptides for binding to PCNA and interruption of PCNA-p21 (141–160) complex can be screened. Such peptides could prove useful in assessing p21-mimetic strategies for cancer treatment.

The method of the invention can also be used to identify potential drug targets using the variant of PCNA binding motif of p21$^{waf1/cip1}$. The method comprises the steps of:

(a) incubating a potential therapeutic agent with a cell which contains a reporter construct, cDNA fragment comprising the variant p21$^{waf1/cip1}$-PCNA binding region covalently linked in a cis configuration to a gene encoding an assayable product;

(b) measuring the production of the assayable product, and (c) identifying a potential therapeutic agent which decreases or increases the production by the cell of the assayable product.

Such an agent may suppress or stimulate the growth of tumor cells by activating or inhibiting the expression of variant p21.

This method of screening for therapeutic agents for use in regulating the growth of cells is achieved by regulating the expression of variant p21$^{waf1/cip1}$. The method comprises the steps of:

(a) measuring, in the presence of a test substance, binding of a protein/peptide which specifically binds to the variant p21$^{waf1/cip1}$-PCNA binding region to a DNA molecular sequence selected from the group consisting of nucleotides 144–151;

(b) measuring the binding of the protein/peptide to the DNA molecular sequence in the absence of a test substance; and (c) comparing the measured binding of the protein/peptide in the presence of the test substance to the measured binding of the protein/peptide in the absence of the test substance, a test substance which increases or decreases the amount of binding being a candidate for use in regulating the growth of cells.

The invention also provides a method for screening therapeutic agents in vitro for use in regulating the expression of variant p21$^{waf1/cip1}$. The method comprises the steps of:

(a) measuring in vitro transcription from a transcription construct, the transcription construct comprising a reporter gene which encodes an assayable product and a p21$^{waf1/cip1}$-PCNA binding sequence selected from the group consisting of nucleotides 144–151, the sequence being upstream from and adjacent to the reporter gene, the in vitro transcription being effected in the presence or absence of a test substance;

(b) determining whether transcription of the reporter gene is altered by the presence of the test substance, a test substance which alters the transcription of the reporter gene being a candidate for use in regulating the growth of cells; and (c) designing potential therapeutic agents (drugs, antisense oligonucleotides etc).

The significantly higher occurrence of the above polymorphic variant in esophageal squamous cell carcinoma patients as compared to normal subjects suggests a role in increased cancer susceptibility and provides the basis for designing methods and kits for diagnosing susceptible subjects.

The frequency of $p21^{waf1/cip1}$ variants (codon 149) in ESCCs with wild-type p53 was significantly higher than in tumours with p53 mutations, suggesting that this polymorphism affects the p53 pathway and may play a role in esophageal tumorigenesis.

The association between SNP at codon 149 in $p21^{waf1/cip1}$ gene and esophageal SCCs as well as oral SCCs suggests its broader utility as a risk factor for assessing predisposition to some human cancers.

Loss of cellular $p21^{waf1/cip1}$ has been reported to result in increased apoptotic killing by inoizing radiation (Tian et al., 2000). Thus, it is yet another embodiment of this invention that genotyping cancer patients for $p21^{waf1/cip1}$ codon 149 variant may serve as a predictor of radiosensitivity of tumors.

Summing up, this is the first report on the novel polymorphism at codon 149, low frequency of polymorphism at codon 31, lack of somatic mutations in $p21^{waf1/cip1}$ gene and induction of $p21^{waf1/cip1}$ by p53-dependent and p53-independent pathways in esophageal cancer in the Indian population. Alteration at codon 149 may be of potential clinical relevance since it may alter $p21^{waf1/cip1}$/PCNA interaction, required for inhibition of DNA replication and subsequent activation of mismatch repair.

EXAMPLES

The invention is illustrated by the following examples which should not be construed as limitations on the inventive scope of the invention.

DNA Extraction

Genomic DNA was extracted from peripheral blood mononuclear cells, esophageal tumor and normal tissues by proteinase K digestion and phenol chloroform extraction (Sambrook et al., 1989).

$p21^{waf1/cip1}$ Gene Amplification by Polymerase Chain Reaction (PCR)

The second exon of the $p21^{waf1/cip1}$ gene previously shown to have a high incidence of mutations was amplified by polymerase chain reaction. The following primer sequences were synthesized (Rama Biotechnology Inc., New Delhi, India).

Primer1 (Exon 2-A.  5'-GCG CCA TGT CAG AAC CGG C-3' Fwd.):

Primer2 (Exon 2-A.  5'-GAG AAT CCT GGT CCC TTA C-3' Rev.):

The PCR reaction mixture consisted of 10 µl of 10×PCR buffer, 20 pmoles of each primer, 1.875 mM deoxynucleotide triphosphates, 1.5 units of Taq DNA polymerase (Perkin-Elmer) and 200 ng genomic DNA in a final volume of 100 µl. The PCR conditions were: denaturation at 94° C. for 4 minutes and 35 cycles of (i) denaturation at 94° C. for 30 seconds (ii) annealing at 55° C. for 30 seconds and (iii) primer extension at 72° C. for 30 seconds followed by autoextension at 72° C. for 5 min. After PCR amplification, the products were checked on 2% agarose gels by electrophoresis using the appropriate DNA molecular weight marker (1 kb DNA ladder).

DNA Sequence Analysis

The PCR products were purified using low melting agarose gels by electrophoresis. The purified products were used for direct DNA sequencing using automated DNA sequencer (Applied Biosystems 373 sequencer and ABI Prism terminators). Different types of controls were used in order to verify that the mutated alleles identified are not artifacts of the sequencing assay. All the sequencing data were obtained by sequencing with both the forward and reverse primers. The sequencing data obtained were confirmed twice by performing a complete repeat of the experimental procedure: amplification of stock genomic DNA, PCR amplification, fragment purification and sequencing of both the DNA strands.

Other features, advantages and embodiments of the invention as disclosed herein will be readily apparent to those exercising ordinary skill after reading the foregoing disclosure. In this regard, while specific embodiments of the invention have been described in detail, variations and modifications can be effected without departing from the spirit and scope of the invention as described and claimed.

What is claimed is:

1. A method for detecting a single nucleotide polymorphism in human subjects having or at risk of having esophageal cancer, said polymorphism being indicative of risk of esophageal cancer, the method comprising:
   a) amplifying a target nuclei acid in DNA isolated from a specimen of a subject;
   b) purifying the PCR products;
   c) DNA sequencing of the PCR products;
   d) detecting single nucleotide polymorphism in $p21^{waf1/cip1}$ gene by determining codon 149 G$\underline{A}$T→G$\underline{GT}$ transition, or by observing the presence or absence of the codon 149 transition, wherein the transition is a polymorphism that is indicative of risk of esophageal cancer.

2. A method as claimed in claim 1, wherein in the target nucleic acid is DNA.

3. A method as claimed in claim 1, wherein the reagents are oligonucleotides.

4. A method as claimed in claim 1, wherein the target nucleic acid is amplified prior to detection.

5. A method as claimed in claim 1, wherein the amplification is effected by polymerase chain reaction (PCR) using specific oligonucleotide primers.

6. A method as claimed in claim 1, wherein the specimen comprises test sample selected from the group consisting of blood, normal tissue and tumor tissue.

7. A method according to claim 1, wherein the polymerase chain reaction (PCR) products are purified using agarose gels, and the DNA sequencing of the PCR products use both forward and reverse primers.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Primer used in PCR to amplify the second
      exon of the p21waf1/cip1 gene. Synthesized by Rama
      Biotechnology Inc, New Delhi, India.

<400> SEQUENCE: 1

-continued

```
gcgccatgtc agaaccggc                                          19

<210> SEQ ID NO 2
<211> LENGTH: 19
<212> TYPE: DNA
<213> ORGANISM: Artificial Sequence
<220> FEATURE:
<223> OTHER INFORMATION: Primer used in PCR to amplify second exon
      of the p21waf1/cip1 gene. Synthesized by Rama Biotechnology,
      Inc., New Delhi, India.

<400> SEQUENCE: 2
gagaatcctg gtcccttac                                          19
```